(12) United States Patent
Logan, Jr. et al.

(10) Patent No.: US 8,829,440 B2
(45) Date of Patent: Sep. 9, 2014

(54) TERAHERTZ FREQUENCY DOMAIN SPECTROMETER WITH DISCRETE COARSE AND FINE TUNING

(71) Applicants: Ronald T. Logan, Jr., Pasadena, CA (US); Joseph R. Demers, North Hollywood, CA (US)

(72) Inventors: Ronald T. Logan, Jr., Pasadena, CA (US); Joseph R. Demers, North Hollywood, CA (US)

(73) Assignee: Emcore Corporation, Albuquerque, NM (US)

( * ) Notice: Subject to any disclaimer, the term of this patent is extended or adjusted under 35 U.S.C. 154(b) by 0 days.

(21) Appl. No.: 13/831,438

(22) Filed: Mar. 14, 2013

(65) Prior Publication Data

US 2013/0200263 A1    Aug. 8, 2013

Related U.S. Application Data

(60) Division of application No. 12/861,651, filed on Aug. 23, 2010, which is a continuation-in-part of application No. 12/465,219, filed on May 13, 2009, now Pat. No. 7,781,736.

(60) Provisional application No. 61/054,344, filed on May 19, 2008.

(51) Int. Cl.
*G01N 21/35* (2014.01)
*A61B 5/05* (2006.01)

(52) U.S. Cl.
CPC ........ *G01N 21/3581* (2013.01); *G01N 21/3586* (2013.01); *A61B 5/0507* (2013.01)
USPC .................................... 250/339.07

(58) Field of Classification Search
CPC ........... G01N 21/3581; G01N 21/3586; A61B 5/0507
USPC ...................................... 250/339.07; 356/300
See application file for complete search history.

(56) References Cited

U.S. PATENT DOCUMENTS

| 4,594,511 A | 6/1986 | Cooper et al. |
| 5,379,110 A * | 1/1995 | Matsui et al. ................. 356/445 |
| 5,379,309 A | 1/1995 | Logan, Jr. |

(Continued)

FOREIGN PATENT DOCUMENTS

| EP | 1 233 527 A1 | 8/2002 |
| GB | 2 381 121 A | 4/2003 |
| WO | WO 2007/135382 A2 | 11/2007 |
| WO | WO 2009/082820 A1 | 7/2009 |

OTHER PUBLICATIONS

U.S. Appl. No. 61/054,344, filed May 19, 2008, Logan, Jr. et al.

(Continued)

*Primary Examiner* — Casey Bryant

(57) ABSTRACT

An apparatus for analyzing, identifying or imaging an target including first and second laser beams coupled to a pair of photoconductive switches to produce CW signals in one or more bands in a range of frequencies greater than 100 GHz focused on and transmitted through or reflected from the target; and a detector for acquiring spectral information from signals received from the target and using a multi-spectral heterodyne process to generate an electrical signal representative of some characteristics of the target. The lasers are tuned to different frequencies and a frequency shifter in the path of one laser beam allows the terahertz beam to be finely adjusted in one or more selected frequency bands.

14 Claims, 4 Drawing Sheets

(56) References Cited

U.S. PATENT DOCUMENTS

| | | | |
|---|---|---|---|
| 5,623,145 | A | 4/1997 | Nuss |
| 6,304,219 | B1 | 10/2001 | Rothe et al. |
| 6,348,683 | B1 * | 2/2002 | Verghese et al. ............ 250/214.1 |
| 6,434,496 | B1 * | 8/2002 | Dong et al. ..................... 702/77 |
| 6,545,785 | B1 | 4/2003 | Heflinger et al. |
| 6,811,552 | B2 | 11/2004 | Weil, Sr. et al. |
| 6,816,647 | B1 | 11/2004 | Rudd et al. |
| 6,844,552 | B2 | 1/2005 | Zhang et al. |
| 6,849,852 | B2 | 2/2005 | Williamson |
| 6,865,014 | B2 | 3/2005 | Ciesla et al. |
| 7,126,078 | B2 | 10/2006 | Demers et al. |
| 7,174,037 | B2 | 2/2007 | Arnone et al. |
| 7,244,934 | B2 | 7/2007 | Arnone et al. |
| 7,291,835 | B2 | 11/2007 | Overney |
| 7,291,839 | B1 * | 11/2007 | Demers et al. ............. 250/341.1 |
| 7,439,511 | B2 | 10/2008 | Demers |
| 7,485,863 | B2 | 2/2009 | Cole |
| 7,535,005 | B2 | 5/2009 | Demers |
| 7,781,736 | B2 | 8/2010 | Logan, Jr. et al. |
| 7,936,453 | B2 | 5/2011 | Logan, Jr. et al. |
| 8,138,477 | B2 | 3/2012 | Gregory |
| 8,604,433 | B2 | 12/2013 | Logan, Jr. et al. |
| 2003/0155512 | A1 | 8/2003 | Arnone et al. |
| 2004/0065831 | A1 | 4/2004 | Federici et al. |
| 2005/0162658 | A1 | 7/2005 | Pepper |
| 2006/0084180 | A1 * | 4/2006 | Paldus et al. .................. 436/171 |
| 2006/0214107 | A1 | 9/2006 | Mueller |
| 2006/0255277 | A1 | 11/2006 | Cole et al. |
| 2008/0179528 | A1 | 7/2008 | Demers |
| 2008/0212974 | A1 | 9/2008 | Davies et al. |
| 2009/0015843 | A1 | 1/2009 | Demers et al. |
| 2009/0066948 | A1 | 3/2009 | Karpowicz et al. |
| 2009/0180122 | A1 | 7/2009 | Federici |
| 2009/0200472 | A1 * | 8/2009 | Gregory ................... 250/339.07 |
| 2010/0080505 | A1 | 4/2010 | Sartorius et al. |
| 2010/0092183 | A1 | 4/2010 | Kim et al. |
| 2011/0032955 | A1 | 2/2011 | Daiber |
| 2014/0043612 | A1 | 2/2014 | Logan, Jr. et al. |

OTHER PUBLICATIONS

Arnone et al., "Applications of Terahertz (THz) Technology to Medical Imaging," *Proc. SPIE Terahertz Spectroscopy Applicat. II*, 1999; 3823:209-219.

Arnone et al., "Terahertz Imaging Comes Into View," *Phys. World*, 2000; pp. 35-40.

Bartels et al., "Femtosecond Time-Resolved Optical Pump-Probe Spectroscopy at Kilo Rates Over Nanosecond-Time-Delays Without Mechanical Delay Line," *Appl. Phys. Lett.*, 2006; 88:04117.

Bartels et al., "High-Resolution THz Spectrometer with kHz Scan Rates," *Optics Express*, 2006; 14(1):430-437.

Bjanason et al., "ErAs:GaAs Photomixer with two decade tenability and 12 μW Peak Output," *Applied Physics Letters*, Nov. 1, 2004; 85(18):3983-3985.

Brown et al., "Characterization of a Planar Self-Complementary Square-Spiral Antenna in the THz Region," *Microwave and Optical Technology Letters*, Mar. 2006; 48(3):524-529.

Chang et al., "Power Scalable Compact THz System Based on an Ultrafast Yb-doped Fiber Amplifier," *Optics Express*, 2006; 14(17):7909-7913.

Chen et al., "Spectroscopic Applications and Frequency Locking of THz Photomixing with Distributed-Bragg-Reflector Diode Lasers in Low-Temperature-Grown GaAs," *Appl. Phys. Lett.*, 1997; 71(12):1601-1603.

Demers et al., "An Optically Integrated Coherent Frequency-Domain THz Spectrometer with Signal-to-Noise Ratio up to 80 dB," 2007 IEEE Conference; pp. 92-95.

Gutierrez, "An Electro-Optical Frequency Shifter," NASA's Jet Propulsion Laboratory, 2000; Available at <URL:http://www.nasatech.com/Briefs/Sept00/NPO20531.html>.

Hu et al., "Imaging with Terahertz Waves," *Optics Letters*, 1995; 20(16):1716-1718.

Hunsche et al., "Terahertz 'T-Ray' Tomography," *Proc. SPIE Int. Millimeter Submillimeter Waves Applicat. IV.*, 1998; 50(3):426-433.

Izutsu et al., *IEEE Journal of Quantum Electronics, QE-17*; Nov. 1991, pp. 2225-2227.

Janke et al., "Asynchronous Optical Sampling for High-Speed Characterization of Integrated Resonant Terahertz Sensors," *Optics Letters*, 2005; 3 0(11):1405-1407.

Jiang et al., "Terahertz Imaging via Eletrooptic Effect," *IEEE Trans. Microwave Theory Tech.*, 1999; 47:2644-2650.

McGrath et al., "Superconductive Hot Electron Mixers with Ultra Wide RF Bandwidth for Heterodyne Receiver Applications Up to 3 THz," *Proceedings of the ESA Symposium*, 1997; pp. 401-404.

McIntosh et al., "Terahertz Measurements of Resonant Planar Antennas Coupled to Low-Temperature-Grown GaAs Photomixers," *Appl. Phys. Lett.*, 1996; 69(24):3632-3634.

Mittleman et al., "T-Ray Imaging," *IEEE J. Select. Topics Quantum Electron*, 1996; 2:679-692.

Saleh et al., "Fundamentals of Photonics," Wiley-Interscience, 1991; pp. 719-720, 823-825.

Search Report for Application No. GB1017046.2 dated Nov. 16, 2010, Intellectual Property Office, UK; 1 page.

Siegel, "Terahertz Technology," *IEEE Transactions on Microwave Theory and Techniques*, 2002; 50(3):915-917.

Verghese et al., "Generation and Detection of Coherent Terahertz Waves Using Two Photomixers," *Applied Physics Letters*, 1998; 73(26):3824-3826.

Wu et al., "Two-Dimensional Electro-Optic Imaging of THz Beams," *Appl. Phys. Lett.*, 1996; 69(8):1026-1028.

Yasui et al., "Terahertz Frequency Comb by Multifrequency-Heterodyning Photoconductive Detection for High-Accuracy, High Resolution Terahertz Spectroscopy," *Applied Physics Letters*, 2006; 88(241104):1-3.

\* cited by examiner

TERAHERTZ FREQUENCY DOMAIN SPECTROMETER WITH DISCRETE COARSE AND FINE TUNING

REFERENCE TO RELATED APPLICATIONS

This application is a divisional of U.S. patent application Ser. No. 12/861,651, filed Aug. 23, 2010, which is a continuation-in-part of U.S. patent application Ser. No. 12/465,219, filed May 13, 2009, now U.S. Pat. No. 7,781,736, which application claims priority of U.S. Provisional Application Ser. No. 61/054,344 filed May 19, 2008. Each of these applications is herein incorporated by reference in its entirety.

This application is related to U.S. patent application Ser. No. 12/062,772, filed Apr. 4, 2008, now U.S. Pat. No. 7,936,453.

This application is also related to U.S. patent application Ser. No. 11/796,069, filed Apr. 26, 2007, now U.S. Pat. No. 7,439,511, which is a continuation-in-part of U.S. patent application Ser. No. 11/669,685 filed Jan. 31, 2007, now U.S. Pat. No. 7,535,005.

BACKGROUND OF THE INVENTION

1. Field of the Invention

The invention relates to microwave, millimeter wave and submillimeter wave spectroscopy systems and components and in particular to an apparatus and method for accurately adjusting the frequency of one or both of the optical beams used in a transceiver for terahertz spectroscopy.

2. Description of the Related Art

Terahertz devices and systems generally employ electromagnetic energy between 300 GHz and 3 terahertz (3 THz), or wavelengths from 100 to 1000 microns (0.1 to 1.0 millimeters), which is also referred to as the submillimeter or far-infrared region of the electromagnetic spectrum.

One important application of terahertz systems is THz spectroscopy. Terahertz spectroscopy presents many new instrumentation and measurement applications since certain compounds and objects can be identified and characterized by a frequency-dependent absorption, dispersion, and/or reflection of terahertz signals which pass through or are reflected from the compound or object.

The generation of terahertz radiation by photomixing is a method of generating quasi-optical signals using an optical-heterodyne converter or photomixer. Typical photomixer devices include low-temperature-grown (LTG) GaAs semiconductor devices, which have been used to generate coherent radiation at frequencies up to 5 THz. The spectroscopy system typically uses two single frequency tunable lasers, such as diode lasers, to generate two optical laser beams which are directed at the surface of the photomixer. By photoconductive mixing of the two beams in the semiconductor material, a terahertz difference frequency between the two optical laser frequencies is generated. In particular, a first laser generates radiation at a first frequency and a second laser generates radiation at a second frequency. The difference frequency, equal to the difference between the first and the second laser frequencies, is swept by the user from microwave through terahertz frequencies by changing the temperature of the lasers, which coarsely changes the frequency of one or both lasers. Other types of tuning mechanisms exist, such as distributed-Bragg-reflector diode lasers with multiple electrodes, grating-loaded external cavities, etc. A terahertz transmitter includes a first photomixer that is optically coupled to the first and the second light source. A first radiative element or antenna is electrically coupled to the first photomixer. In operation, the first antenna radiates a terahertz signal generated by the first photomixer at the difference frequency. A receiver includes a second antenna positioned to receive the signal from the target radiated by the first antenna. The second antenna generates a time varying voltage proportional to the terahertz return signal. A second photomixer is electrically coupled to the second antenna and is optically coupled to the first and the second light source. The second photomixer generates a homodyne downconverted current signal in response to the time varying voltage generated by the second antenna. The downconverted signal is a measurement of the absorption or reflection of the material at each terahertz frequency. This is useful, for example, when used in conjunction with computer processing to identify unknown samples by comparing measured results to a library of reference spectra. This apparatus may also be used to characterize the frequency response characteristics of passive or active components and devices such as waveguides, filters, amplifiers, mixers, diodes, and the like designed to work at terahertz frequencies.

SUMMARY OF THE INVENTION

1. Objects of the Invention

It is an object of the present invention to provide an improved frequency domain terahertz spectrometer using two continuously tunable semiconductor lasers with the relative frequency of the optical beam applied to respective source and detector photoconductive switches being electronically adjustable.

It is another object of the present invention to provide a terahertz spectrometer for the identification of a target spectrum with high resolution and detection sensitivity of absorption bands of interest by producing CW radiation in one or more frequency bands, and "fine tuning" the terahertz radiation in at least some of those bands to identify a spectral signature.

It is also another object of the present invention to mitigate the interference effect in a frequency domain terahertz spectrometer with finely controllable frequency.

It is an object of the present invention to provide a method for independently coarsely and finely adjusting the frequency difference between two source lasers forming a composite optical beam used in a frequency domain terahertz spectrometer.

It is another object of the present invention to provide a method for adjusting the frequency of a laser in a terahertz spectrometer using photoconductive switches to provide more accurate frequency specificity and resolution by "fine tuning" the terahertz radiation in a frequency band of interest using a reference oscillator.

It is also another object of the present invention to provide a terahertz spectrometer with adjustable resolution of the order of Hz or 10's of Hz at specific frequency bands or absorption regions of interest.

It is another object of the present invention to provide a method for adjusting the frequency of a laser in a terahertz spectrometer using photoconductive switches to provide more accurate frequency specificity and resolution by first "coarsely tuning", and then subsequently "fine tuning" the terahertz radiation in a frequency band of interest.

It is another object of the present invention to provide a method for adjusting the frequency of a laser in a terahertz spectrometer using photoconductive switches to provide more accurate frequency specificity and resolution by "fine tuning" the terahertz radiation in a frequency band of interest.

It is still another object of the present invention to provide a self-contained, field portable terahertz spectrometer system in a highly compact configuration capable of identifying or imaging an object utilizing a laser with an electronically adjustable or controllable frequency.

It is still another object of the present invention to provide a field portable terahertz spectrometer system with separately packaged source and detector heads which may be manually positioned by the operator.

Some implementations may achieve fewer than all of the foregoing objects.

2. Features of the Invention

Briefly, and in general terms, the present disclosure provides an apparatus for analyzing, identifying or imaging a target, including a first housing including first and second lasers having tunable frequencies and coupled to first and second optical fibers respectively; a second housing including (i) a first photoconductive switch activated by an optical beam from the first optical fiber for producing electromagnetic radiation in a range of frequencies greater than 100 GHz, and (ii) a radiator for directing said radiation to a target; and a third housing including (i) a receiver for acquiring electromagnetic radiation in a range of frequencies greater than 100 GHz from the target, and (ii) a second photoconductive switch activated by an optical beam from the second optical fiber and coupled to the electromagnetic radiation from the receiver and functioning to generate an electrical signal representative of some characteristic of the target.

In another aspect, the disclosure provides an apparatus for analyzing, identifying or imaging an object, including a source of CW signals in a range of frequencies greater than 100 GHz directed to said object; and a detector for acquiring spectral information reflected from or transmitted through said object and performing a heterodyne downconversion for generating an electrical signal representative of some characteristics of the object.

In another aspect, the disclosure provides a method for analyzing, identifying or imaging an object, including generating CW signals in a range of frequencies lying above 100 GHz and directing them to said object; and acquiring spectral information reflected from or transmitted through said object and performing a heterodyne downconversion for generating an electrical signal representative of some characteristics of the object.

In another aspect, the disclosure provides a method for analyzing, identifying or imaging a target by providing first and second lasers having first and second output beams respectively having different frequencies; frequency shifting the first output beam to produce a third beam; generating a CW radiative beam using a first photoconductive switch in the range of frequencies greater than 100 GHz from the first and third beams; causing the CW radiative beam to be substantially simultaneously focused on or through the target; combining the first beam and the second beam into a composite fourth beam; acquiring a spectral information signal from said target using a second photoconductive switch activated by said composite fourth beam; and generating an electrical signal representative of a characteristic of said target using said spectral information signal and said composite fourth beam.

In another aspect, the disclosure provides a method comprising providing first and second lasers having tunable frequencies for producing a first optical beam and a second optical beam respectively with different frequencies; frequency shifting or modulating the first optical beam to produce a finely adjustable frequency shifted third optical beam; producing a composite fourth beam from the second and the third optical beams; producing a composite fifth beam from the first and the second optical beams; coupling the fourth optical beam to a first photoconductive switch for producing a CW radiative beam in a range of frequencies greater than 100 GHz; directing the CW radiative beam to be focused on or through a target; and detecting the radiative beam reflected from or transmitted through the target by a second photoconductive switch coupled to the composite fifth optical beam; and generating an electrical signal representative of some characteristic of the target.

In another aspect, the disclosure provides a method for terahertz spectroscopy including sweeping a source of CW radiative beams over a range of frequencies greater than 100 GHz, including a first photoconductive switch activated by a first composite optical laser beam; directing the radiative beam to be focused on a target; and acquiring spectral information from the target by a second photoconductive switch coupled to a second composite optical beam; and finely adjusting the frequency difference between the first composite beam and the second composite optical beam by a frequency modulator in the path of one of the first and second optical beams used to generate the first composite optical beam, for generating additional electrical signals representative of some characteristic of the target in a selected frequency band.

In another aspect, the disclosure provides a method for terahertz spectroscopy including sweeping a source of CW radiative beams in one or more predetermined frequency bands lying in a range of frequencies greater than 100 GHz; acquiring spectral information from the target; and processing the spectral information to determine the presence of a specific spectral signature to identify a compound of interest.

In another aspect, the disclosure provides a method for identifying a compound in a target using terahertz spectroscopy by storing a spectral signature of the predetermined compound; sweeping a CW radiative beam over at least one frequency band in the range of frequencies greater than 100 GHz; directing the radiative beam to a target; acquiring spectral information from the target; and determining whether the spectral signature of the predetermined compound is present in the acquired spectral information by tuning the frequency of the CW radiative beam in frequency increments of less than 100 MHz in the frequency region of the spectral signature.

Some implementations or embodiments may incorporate or implement fewer of the aspects or features noted in the foregoing summaries.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein.

Figure 1A:
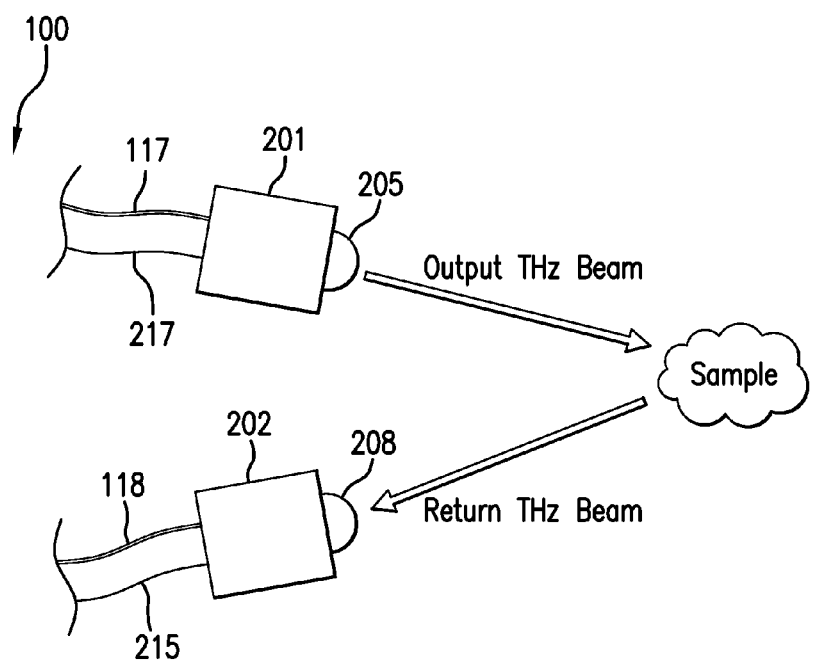
FIG. 1A is a block diagram of a frequency domain terahertz spectrometer according to the present disclosure which employs reflection from the sample.

The novel features and characteristics of the disclosure are set forth in the appended claims.

DETAILED DESCRIPTION OF THE PREFERRED EMBODIMENT

Details of the present disclosure will now be described, including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As noted above, in the frequency domain technique for terahertz spectroscopy, CW THz radiation is produced through photomixing of the combined output of two single-frequency diode lasers in a low temperature grown GaAs photomixer or PCS. The wavelength of one (or both) of the lasers is tuned by temperature adjustment of the laser to coarsely vary the THz output frequency, which may therefore be swept over one or more frequency bands of interest for characterizing the target or sample material.

In most frequency domain spectrometers, coherent (homodyne) detection can be achieved at room temperature by mixing the same optical radiation from the diode lasers in a detector PCS onto which the return THz signal is also incident. This provides similar or greater sensitivity and faster data acquisition than the incoherent technique.

Figure 1B:
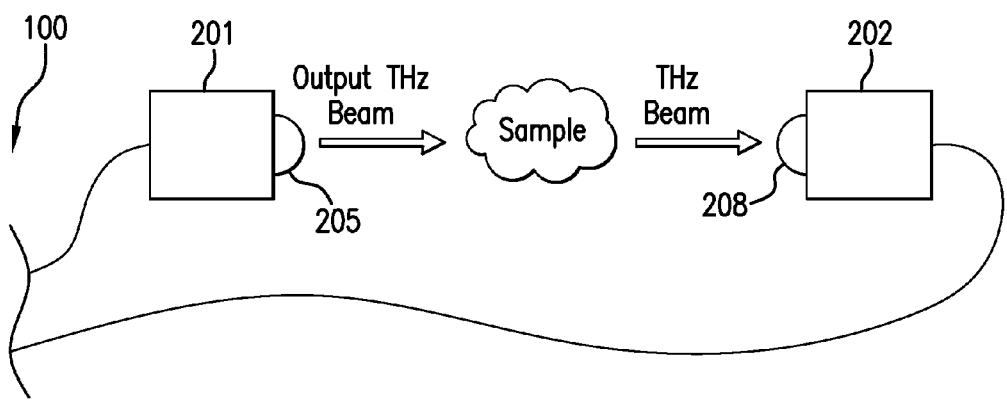
FIG. 1B is a block diagram of a frequency domain terahertz spectrometer according to the present disclosure which employs transmission from the sample.

In a terahertz spectrometer, the terahertz radiation is focused or directed to the target sample to be analyzed, and a detector or detector array is arranged to collect the signal propagated through or reflected from that target. The two modes of transmission or reflection from the target are illustrated in FIGS. 1A and 1B. The configuration or arrangement of FIG. 1A depicts reflection, and FIG. 1B depicts transmission through the target or sample by appropriate placement of the source head or module 201 and the detector head or module 202. A housing 100 (shown in FIG. 2) incorporates the user interface and the optical and electro-optical components associated with the coupled spectrometer heads of FIGS. 1A and 1B. In one embodiment of the present disclosure, the modules 201 and 202 are enclosed in different housings, each of which may be manually moved or positioned by the operator with respect to the sample under test. A fiber optic cable 117 and an electrical cable 217 couple the housing 100 to the module 201, and fiber optic cable 118 and an electrical cable 215 couple the housing 100 to the module 202. The silicon lens 205 on the exterior of the housing 201 enables the terahertz radiation to be focused or directed to the target by the user, and the silicon lens 208 on the exterior of the housing 202 is positioned by the user so that it collects the radiation transmitted or reflected from the target. It is noted that additional optical elements including but not limited to lenses, focusing mirrors, parabolic reflectors, sub-reflectors, beam-splitters/combiners, and beam-shaping optics (not shown for clarity) may also be employed to provide focusing or manipulation of the radiated terahertz beams, as the particular measurement situation requires.

FIG. 1B is a block diagram of a representative spectrometer arranged to employ transmission through the sample. The operation of the various components are substantially identical to the operation in FIG. 1A, and need not be repeated here. The figure illustrates how the source and detector housings 201 and 202 may be manually moved and positioned by the operator with respect to the target. Alternatively, the source and detector housings 201 and 202 may be combined into one common housing.

Figure 2:
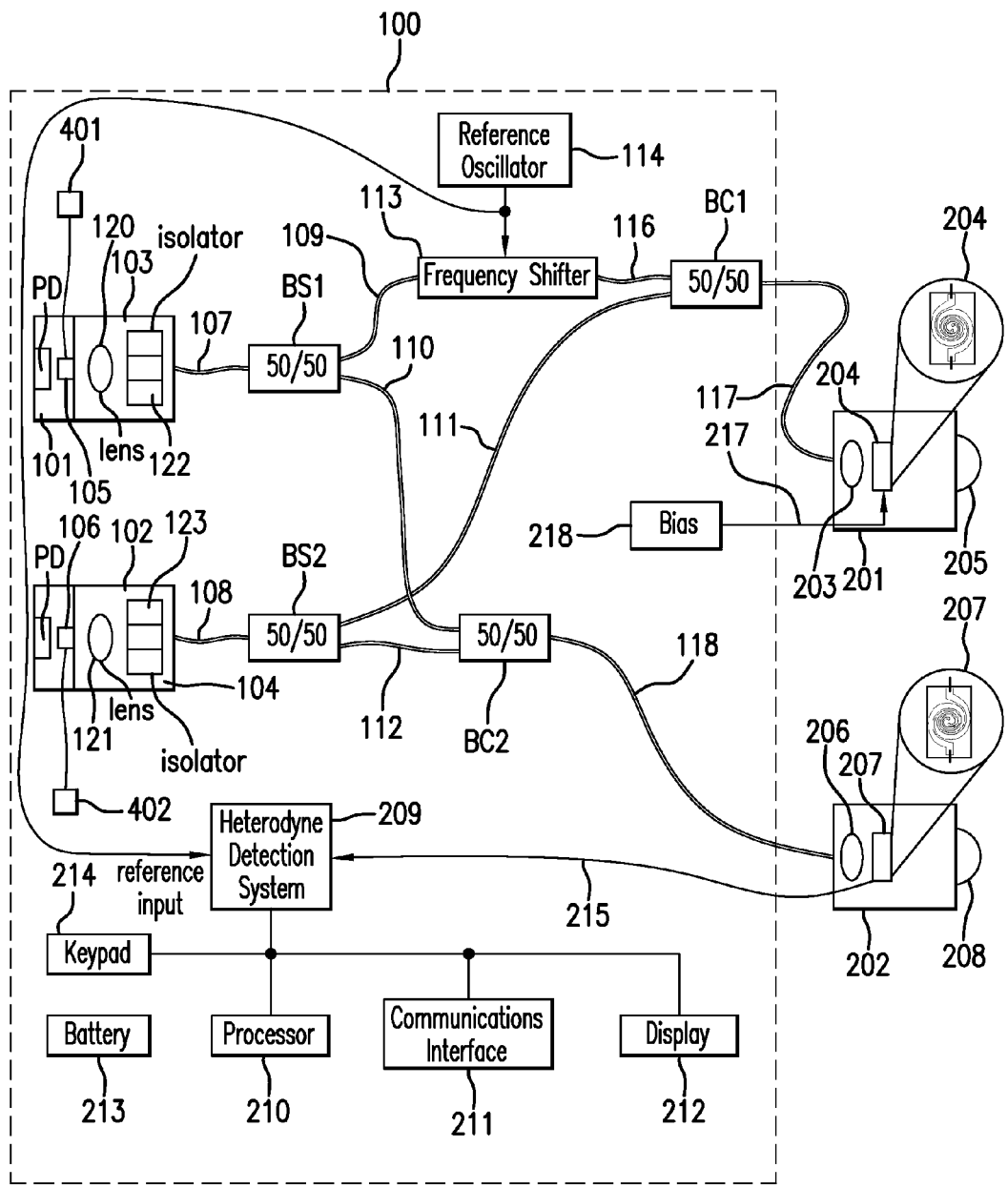
FIG. 2 is a block diagram of a frequency domain terahertz spectrometer of the present disclosure.

Turning to FIG. 2, there is depicted a housing 100 incorporating the optical and electro-optical components suited for use as a subassembly in conjunction with the coupled spectrometer heads of FIGS. 1A and 1B. In some embodiments, the housing is sized and designed to be lightweight and portable, and worn or supported by the user during operation. Laser subassemblies 101 and 102 include lasers 105 and 106, respectively, which are preferably two 783 nm distributed feedback (DFB) or distributed Bragg reflector (DBR) semiconductor laser diodes with single-longitudinal-mode and single spatial-mode operation over the desired range of wavelengths, available from various vendors (for example, Eagleyard Photonics GmbH of Berlin, Germany, or Photodigm, Inc. of Richardson, Tex.). In some embodiments it would also be possible to utilize one or more packaged external-cavity tunable semiconductor lasers such as are available from Emcore Corporation, of Newark, Calif., such as disclosed in U.S. patent application Ser. No. 12/722,825, filed Mar. 12, 2010. In one embodiment, the output of one laser is adjusted to 783 nm, and the output of the other laser is adjusted to 784 nm. The diode laser packaging permits co-collimation of the laser beams to a very high degree of precision, and the design allows very precise frequency control of the lasers by temperature and/or electronic tuning, and monitoring the laser output through digital signal processing, to achieve more accurate control over the laser output beam frequencies.

In one embodiment, the laser diode chips 105 and 106 are mounted on independent Peltier thermoelectric coolers (TECs) 103 and 104. The center wavelengths of the lasers are nominally 783 nm at 25° C., but the wavelengths may be coarsely temperature-tuned with a tuning coefficient of approximately 0.1 nm per ° C. Therefore, a 50 degree C. temperature range of operation from −10 degrees C. to +40 degrees C. will yield a frequency range of approximately 5 nm. For the purposes of illustration only, if the DFB lasers are selected such that their center wavelengths at 25 degrees C. are at 782 nm and 784 nm, respectively, then a thermal tuning range of −10 degrees C. to +40 degrees C. on each laser chip will permit generation of offset wavelengths 0 nm to approximately 7 nm, corresponding to a range of offset frequencies from 0 Hz to 3.4 THz. The thermal mass on the controlled surface of the TECs is such that it allows rapid frequency tuning. In the case of DBR laser diode chips, the Bragg-reflection section of each laser may be adjusted electronically to vary the laser frequency. Wider offset frequency ranges may also be possible by employing wider temperature excursion, or by using DBR or external cavity lasers.

The output beam from each laser 105, 106 is collimated with an aspheric lens 120, 121 respectively, mounted on a precision lens-mount with sub-micron adjustment capability (see, e.g. U.S. Pat. No. 7,126,078). After passing through the lens, the laser output beams are directed through a respective optical isolator 122 and 123, to prevent feedback into the laser, and to couple the output beam to pigtail optical fibers 107 and 108, respectively.

FIG. 2 also depicts an aspect in some embodiments of the spectrometer system including a first current source 401 which is coupled to laser 105 to drive it and modulate it with a low frequency 416 kHz tone, and a second current source 402 which is coupled to laser 106 to drive it and modulate it with a second low frequency 430 kHz tone. The use of such tones in connection with the composite optical signal is discussed in U.S. patent application Ser. No. 12/062,772 filed Apr. 4, 2008. Other tone frequencies may be selected as convenient or appropriate for the intended application.

A 50/50 waveguide coupler or beamsplitter BS1 and BS2 are coupled to the pigtail optical fibers 107 and 108, respectively, and the output beams on fibers 107 and 108 are each split into composite primary and secondary beams 109 and 110, and 111 and 112 respectively.

In the embodiment depicted in the present disclosure, the primary output beam 109 is directed along a fiber or first path to a frequency control element such as a frequency shifter 113 or frequency modulator (which performs a frequency shifting function by creating sidebands that are shifted or offset from the original center frequency). The frequency shifter 113 may be an acousto-optical device, such as those manufactured by Brimrose Corporation of America, Inc., of Sparks, Md. Alternatively, one may also use a single-sideband frequency-shifter such as described by Izutsu, M. et al in the IEEE Journal of Quantum Electronics, QE-17, pp. 2225-2227, November 1981. The frequency shifter 113 allows the user to automatically (by pre-programmed software) or manually adjust the frequency of the laser output beam 109 in a highly precise manner, thereby also adjusting the frequency of the emitted CW terahertz beam. The output of the frequency shifter 113 is then coupled to a waveguide coupler or beamcombiner BC1.

A tunable reference oscillator 114 is connected to the frequency shifter 113 for precisely incrementing or decrementing the frequency.

The beam 110 is directed along a fiber or first path to a waveguide coupler or beamcombiner BC2, and similarly the beam 112 is directed along a fiber or first path to the waveguide coupler or beamcombiner BC2. The output beam from beamsplitter BS2 is directed along a fiber 118 or first path so as to exit the module 100 and is subsequently directed by fiber 118 to the detector head 202.

The output beam 111 from beamsplitter BS2 is directed along a fiber or first path to the beamcombiner BC1. The output of the frequency shifter 113 is directed along fiber 116 to the beamcombiner BC1. The output of beamcombiner BC1 is then applied to fiber 117 which exits the module 100 and is subsequently directed to the source head 201.

The optical propagation path downstream of the lasers and throughout the unit 100 may be an appropriate single-mode polarization-maintaining optical fiber (PMF) or free space. In the case of optical fiber construction, the beamsplitters may be replaced with suitable optical waveguide couplers. As can be appreciated, the basic topology depicted in FIG. 2 uses fiber optical implementation which readily illustrates the various optical paths, while FIG. 4 will illustrate a free space implementation.

The beam from beamcombiner BC1 is coupled to a fiber 117 which is then coupled to the external source head 201, as described above. In source head 201, the composite output beam of the two distinct laser sources is then applied to a lens 203 which focuses the beam to a spot of approximately ten microns in diameter on the surface of a low temperature grown (LTG) gallium arsenide (GaAs) photoconductive switch (PCS) 204. The two optical beams are combined or photomixed in the PCS 204. Other types of photoconductive switches may be used as well. The laser beam may be focused at a gap in an antenna circuit patterned on the surface of the PCS, which in some embodiments is implemented as the spiral as shown in FIG. 2, with the gap located at the center of the spiral. A constant DC electrical bias coupled to the source head by cable 217 may also be applied across the terminals of the antenna on the PCS. In some embodiments, as known in the prior art, a slowly time-varying (i.e., "chopped") electrical bias signal may be applied across the terminals of the antenna on the PCS.

The terahertz variation in the intensity of the mixing or difference signal between the two laser frequencies, often referred to as the "heterodyne laser signal", produces a terahertz modulation of the conductance in the PCS material, which in turn produces a terahertz current flow in the antenna patterned on the surface of the PCS. This current in the antenna produces an electromagnetic field, i.e. terahertz radiation, propagating into the surrounding space and having a frequency range from typically 100 GHz to over 2 THz, depending on the difference frequency of the two laser sources. The terahertz radiation so produced is emitted from PCS device 204 and then collimated and collected by a silicon lens 205, preferably a hemispherically shaped structure approximately two to three centimeters in diameter. Additional lenses (not shown), composed of TEFLON™ or other suitable materials may be placed downstream of the lens 205 to collimate the RF beams into an output terahertz beam. Beam-shaping mirrors may also be used in lieu of or in addition to the silicon lens 205 in the source head 201.

The outgoing terahertz radiation beam from currently available PCS devices is relatively low power, about 1 to 10 microwatts. The target sample (not shown) is typically positioned relatively close to the source and detector heads, and will absorb and transmit some terahertz radiation, and also reflect a portion of the terahertz radiation back in the direction of the source or user, as shown by the return THz beam in FIG. 1A.

On the receiver side of the spectrometer, the beam from beamcombiner BC2 is coupled to a fiber 118 which is then coupled to the external detector head 202, as described above. In detector head 202, the composite output beam of the two distinct laser sources is then applied to a lens 206 which focuses the beam to a spot of approximately ten microns in diameter on the surface of a low temperature grown (LTG) gallium arsenide (GaAs) photoconductive switch (PCS) 207. The two optical beams are combined or photomixed in the PCS 207. Other types of photoconductive switches may be used as well. The laser beam may be focused at a gap in an antenna circuit patterned on the surface of the PCS 207, which in some embodiments is implemented as the spiral as shown in FIG. 2, with the gap located at the center of the spiral. In some embodiments the spiral antenna on the detector PCS 207 is implemented in a clockwise direction, in contrast to the counter-clockwise direction of the spiral antenna on the source PCS 204.

The terahertz return signal from the sample or target is captured by a suitably positioned second silicon lens 208 in the detector head 202, which focuses the return terahertz beam to the antenna on the surface of PCS 207 which acts as a terahertz radiation detector.

In the prior art embodiments, the terahertz variation in the intensity of the mixing or difference signal between the two laser frequencies, in combination with the terahertz modulation of the conductance in the PCS material, as a result of the terahertz current flow in the antenna from the received terahertz signal from the sample, results in a homodyne downconversion of the received terahertz signal to a baseband frequency equal to the "chopping" frequency, that may then be detected by a synchronous circuit such as a "lock-in" amplifier, or similar arrangement.

In embodiments contemplated by the present disclosure, the terahertz variation in the intensity of the mixing or difference signal between the two laser frequencies, in combination with the terahertz modulation of the conductance in the PCS material as a result of the terahertz current flow in the antenna from the received terahertz signal from the sample, results in a heterodyning and downconversion of the received terahertz signal to a baseband frequency equal to the frequency of the reference oscillator 114. The synchronous detection circuit makes use of the reference oscillator 114 signal applied to the frequency shifter 113, and thereby to the signal applied to source PCS 204, as a reference for the synchronous detection process. In addition, the bias voltage 218 to the source PCS 204 may also be modulated, and supplied to the heterodyne detection system (connection not shown) such that a "lock-in" amplifier configuration can also be employed to improve noise rejection and detection sensitivity.

A signal resulting from this heterodyne detection system 209 may be coupled to and processed by processor 210. The spectrometer may further incorporate software for automatically determining the identity or composition of the target, and other electronic elements for printing or displaying the results so that the analysis, identification, or image information is readily available to the user. FIG. 2 illustrates a communications interface (which may be a wireless RF transceiver for communicating the results to an external user or network element) 211, a display 212, and a keypad 214 as examples of elements providing user or operator interface. A battery 213, or other self-contained power source, may be provided to make the unit field portable.

In one embodiment, the frequency of one of the lasers, and consequentially the radiative terahertz frequency, is swept or tuned through a series of frequencies, or through a sequence of distinct specific frequency bands. The return terahertz signal $S_{out}$ is collected by the detector and transferred to processor 210 for data collection and analysis at each specific frequency of interest. In this way, the absorption or reflection spectrum of the sample under test can be collected with high resolution and high signal-to-noise ratio since all of the terahertz energy is centered in a single tone and the lock-in amplifier limits the noise bandwidth. This, incidentally, is a major advantage of the frequency domain technique compared to time-domain techniques in which the terahertz energy is spread over many frequencies. In some embodiments, the tuning and terahertz emission may be adapted to a specific sequence or set of frequency bands having spectral absorption peaks corresponding to the unique spectral signature of a particular material of concern. Thus, the frequency sweeping time may be minimized if the user's application was solely the question: "Is compound X present in the sample?", since the processor and software in the spectrometer may be pre-programmed to only generate, sweep, record and analyze the terahertz frequency bands associated with the spectral signature of a particular material of concern.

Figure 3:
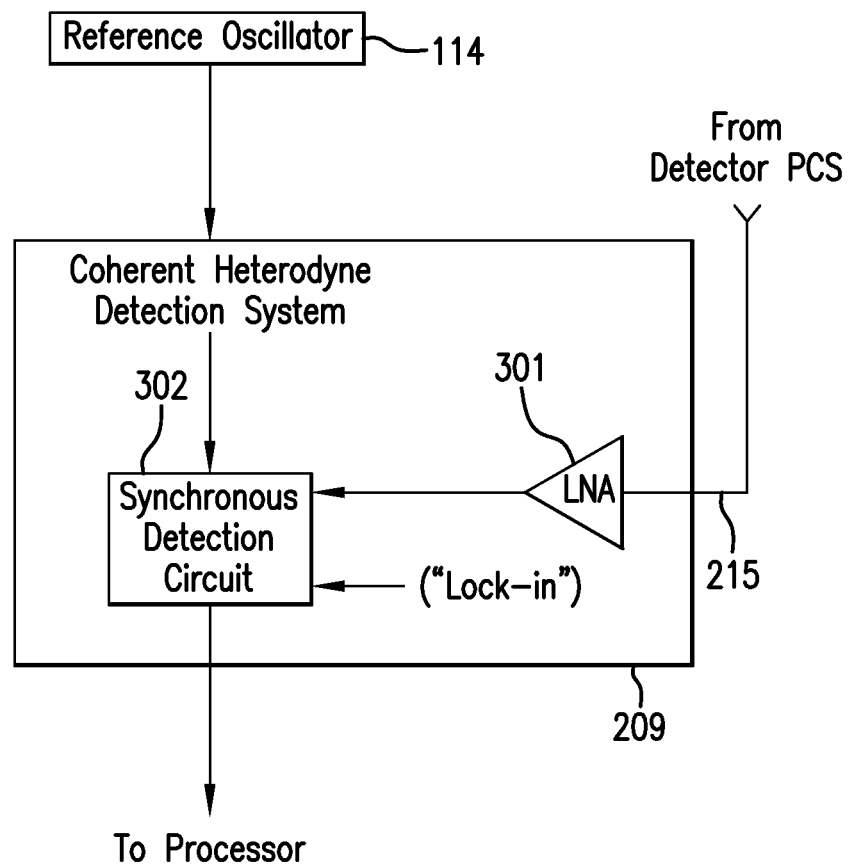
FIG. 3 is a block diagram of a heterodyne detection system subassembly.

FIG. 3 is an enlarged block diagram of a heterodyne detection system subassembly 209 shown in FIG. 2. The reference oscillator 114 provides a reference signal that may be adjusted by the operator between 0 and 10 GHz in selectable step sizes or intervals ranging from 1 Hz to 1 GHz. The signal from the detector PCS is applied on line 215 to a low noise amplifier (LNA) 301, and then to a synchronous detection circuit 302. The downconverted output of the synchronous detection circuit 302 is then forwarded to the processor 210. The optional "lock-in" signal is derived from the bias 218 if this mode of operation is employed, as discussed above.

Figure 4:
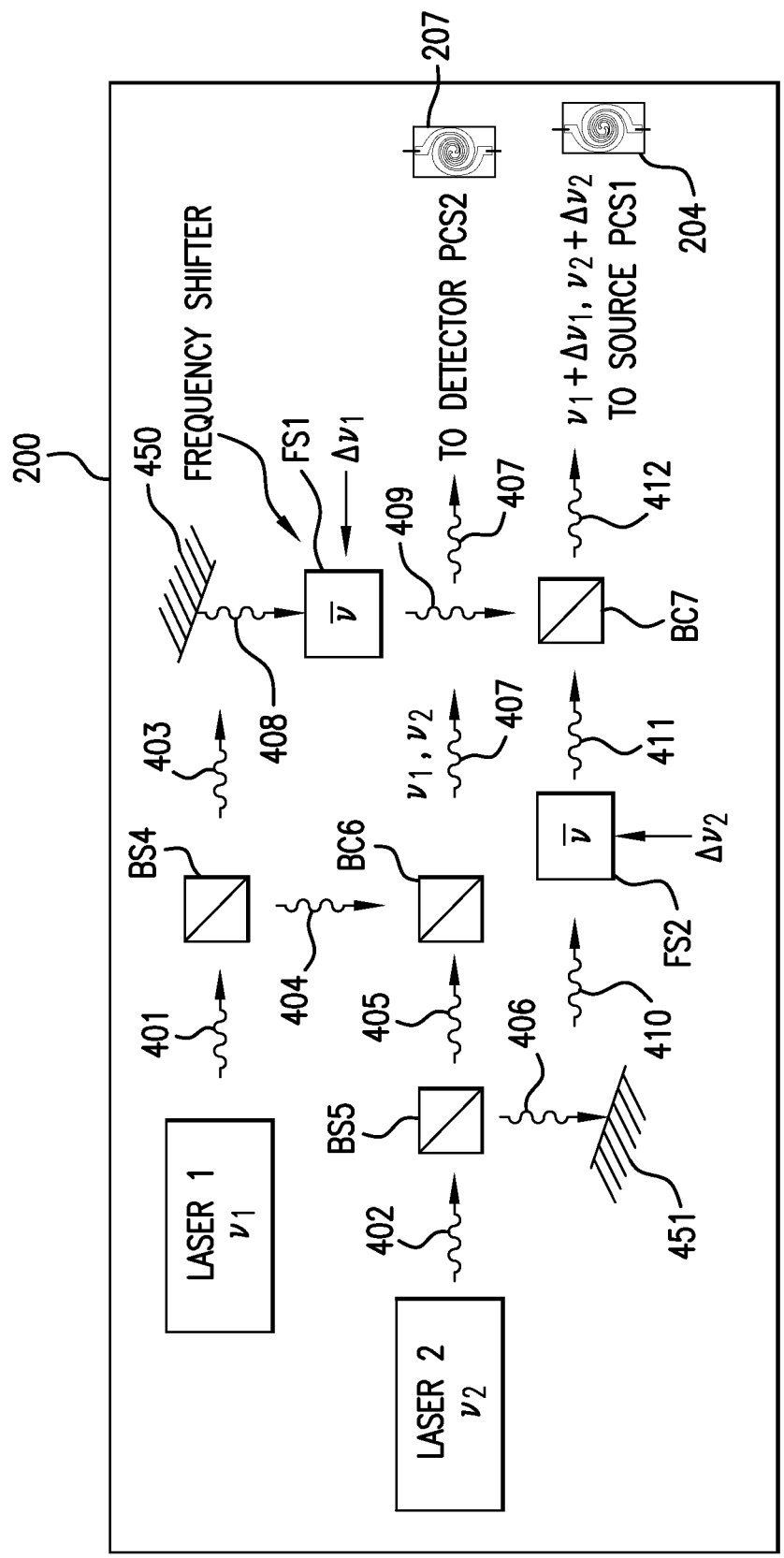
FIG. 4 is a block diagram of a terahertz spectrometer with a frequency shifter according to an embodiment of the present disclosure.

Turning now to FIG. 4, there is shown in schematic form a configuration according to another embodiment and aspect of the present disclosure employing a frequency-shifted, heterodyne detection scheme, employing in one embodiment a second frequency shifter as the source or transmitter portion of the spectrometer. Shown in FIG. 4 are two lasers, Laser 1 and Laser 2, the outputs of which are shown as 401 and 402 at frequencies $v_1$ and $v_2$, respectively. The light output beam from Laser 1 is depicted as beam 401 directed to a beam splitter BS4 where it is split into two beams, 403, 404 respectively.

The split beams 403, 404 output by Laser 1 are directed along separate optical paths. Split beam 403 is directed to a frequency shifter FS1. In some embodiments, geometric or other packaging concerns may make it advantageous to re-direct or focus the beam to frequency shifter FS1 by means of a reflector or other optical element 450. Of course, such redirection—while shown here as preceding the frequency shifter FS1—may in fact be positioned downstream from the frequency shifter FS1 as may be appropriate.

In one embodiment, the frequency shifter FS1 effects a frequency shift of substantially $\Delta v_1$ in the beam 408, thereby resulting in a beam 409 having the frequency $v_1 + \Delta v_1$.

Similarly the light output from Laser 2, beam 402 having a frequency of $v_2$ is directed to a beam splitter BS5 where it is split into two beams, 405, 406 respectively. The split beams 405, 406 output by Laser 2 likewise may be directed along separate optical paths. Split beam 406 is directed to a frequency shifter FS2. As can be appreciated and previously noted, geometric or other packaging concerns may make it advantageous to re-direct or focus the split beams through the effect of mirrors 451 or other optical components which may advantageously produce re-directed split beam 410. Of course, such redirection—while shown here as preceding the frequency shifter FS2—may in fact be positioned downstream from the frequency shifter FS2 as may be appropriate.

In one embodiment, the frequency shifter FS2 effects a frequency shift of substantially $\Delta v_2$ into the beam 410, thereby resulting in a beam 411 substantially at frequency $v_2 + \Delta v_2$. In other words, the original beam 410 at frequency $v_2$ is frequency shifted by an amount $\Delta v_2$ to the frequency of $v_2 + \Delta v_2$.

The two separate, frequency shifted split beams 409 and 411 which originated from Laser 1 and Laser 2 respectively, are combined through the effect of beam combiner BC7 into a combined, frequency shifted beam 412. This combined, frequency shifted beam 412 is a combination of light having frequency $v_1 + \Delta v_e$, and light having frequency $v_2 + \Delta v_2$, and is directed to the detector PCS1 (shown in a top plan view as element 204) to effect the generation of terahertz beam(s) for subsequent irradiation of a target sample.

The other split beams from Laser 1 and Laser 2, namely beam 404 and 405, respectively, are combined through the effect of beam combiner BC6. More particularly individual split beams 404 and 405 are combined through the effect of combiner BC6 into combined beam 407 having both frequencies $v_1$ and $v_2$. This combined beam 407 is then directed to detector PCS2 (shown in a top plan view as element 207).

Although the embodiment depicted in FIG. 4 utilizes two frequency shifters FS1 and FS2, other embodiments may use only a single frequency shifter, associated with either beam 408 or 410.

In summary, certain aspects of the present disclosure may provide a compact frequency domain terahertz coherent spectrometer with either continuous tuning, or discrete tuning within certain identified frequency bands greater than 100 GHz. Such construction may employ highly compact photonic integration techniques, and room-temperature coherent THz detection. Advantageously, such devices may offer rapid identification of chemical, biological and explosive materials in both the solid-phase and the gas-phase at standard atmospheric pressure. Some embodiments may utilize a highly integrated photonic assembly employing semiconductor diode lasers employing no moving parts, so that it is inherently rugged and well-suited to field-deployable applications. The frequency-shifted optical beams are incident on the source PCS (or alternatively, in other embodiments, the detector PCS, or both), and provides a means to effect extremely high-resolution spectroscopy. One may adjust the frequency of the source optical heterodyne signal with finer resolution than is typically possible using thermal control of the lasers alone. Typical thermal tuning resolution and accuracy of the source lasers may perform coarse tuning over a wavelength range up to 15 nm, in intervals or step sizes of about 0.01 nm.

Of course, various modifications and improvements of the present disclosure may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

It will be understood that each of the elements described above, or two or more together, also may find a useful application in other types of constructions differing from the types described above. In particular, certain configurations presented according to particular aspects of the present invention have been shown and described as discrete elements, i.e., lasers, splitters, combiners, mirrors, lenses, shifters, fiber optical cable, etc. Those skilled in the art will readily appreciate that many or all of these individual, discrete components may be fabricated and/or packaged into integrated elements. By way of particular example, the use of integrated waveguides and associated structures is envisioned for the described structures and arrangements. Alternatively, the discrete elements, i.e., lasers, splitters, combiners, mirrors, lenses, shifters, etc. may also be individually-packaged in modules with optical fiber interconnects to achieve the same topology and functionality.

While the present disclosure illustrates and describes a terahertz transceiver or spectrometer system, it is not intended to be limited to the details shown, since various modifications and structural changes may be made without departing in any way from the spirit of the present invention.

Without further analysis, the foregoing others can, by applying current knowledge, readily adapt the disclosed technology for various applications. Such adaptations should and are intended to be comprehended within the meaning and range of equivalence of the following claims.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality.

While particular embodiments of the present invention have been shown and described, it will be understood by those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," "comprise" and variations thereof, such as, "comprises" and "comprising" are to be construed in an open, inclusive sense, that is as "including, but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

What is claimed is:

1. A method for spectroscopy comprising:
   sweeping a CW radiative beam over at least one frequency band in a range of frequencies greater than 100 GHz;
   receiving the CW radiative beam with a frequency control element and finely adjusting the frequency of the CW radiative beam using the frequency control element in frequency increments less than 100 MHz for generating electrical signals representative of some characteristic of a target in the at least one frequency band;

directing the finely adjusted radiative beam to a target; and acquiring spectral information from the target.

2. A method as defined in claim 1, further comprising providing first and second lasers having different tunable frequencies, and wherein sweeping the CW radiative beam includes activating a first photoconductive switch by a first composite optical beam from the first and second lasers, and wherein sweeping a CW radiative beam over at least one frequency band in a range of frequencies greater than 100 GHz comprises sweeping the frequency of one of the first and second lasers.

3. A method as defined in claim 2, further comprising performing a heterodyne down conversion of the acquired spectral information from the target, wherein acquiring spectral information from the target comprises:

activating a second photoconductive switch by a second composite optical beam from the first and second lasers, the second composite beam being different from the first composite beam; and generating an electrical signal representative of radiation transmitted or reflected from the target to provide spectral information from the target.

4. A method as defined in claim 3, further comprising:

biasing the first photoconductive switch with a modulated bias voltage; and providing a "lock-in" amplifier in a detection system coupled to the second photoconductive switch, wherein the modulated bias voltage is supplied to the detection system.

5. A method as defined in claim 2, further comprising providing first and second thermoelectric coolers coupled to the first and second lasers respectively for independently coarsely tuning each of the lasers over a wavelength range of about 5 nm intervals or step sizes of about 0.01 nm.

6. A method as defined in claim 2, wherein the frequency control element comprises a frequency shifter coupled to a portion of an output beam from the first laser for tuning the frequency of the portion of the output beam from the first laser over at least a portion of a frequency range between 0 and 10 GHz.

7. A method as defined in claim 6, further comprising providing a reference oscillator coupled to the frequency shifter for tuning the frequency of the portion of the output beam from the first laser with a frequency interval or step size less than 1 MHz.

8. A method as defined in claim 6, further comprising providing a reference oscillator coupled to the frequency shifter for tuning the frequency of the portion of the output beam from the first laser.

9. A method as defined in claim 8, wherein the reference oscillator has an adjustable frequency interval or step size between 1 Hz and 100 MHz.

10. A method as defined in claim 8, wherein an intensity of a mixing or difference signal between laser frequencies of the first and second lasers, in combination with the modulation of the conductance in the photoconductive switches as a result of current flow in an antenna from the radiation transmitted or reflected from the target, results in a heterodyning and down conversion of an electrical signal representative of radiation transmitted or reflected from the target to provide spectral information from the target to a baseband frequency equal to the frequency of the reference oscillator.

11. A method as defined in claim 2, wherein the frequency control element comprises frequency shifter coupled to a portion of an output beam from the first laser for tuning the frequency of the portion of the output beam from the first laser with an adjustable frequency interval or step size between 1 Hz and 100 MHz.

12. A method as defined in claim 2, wherein the frequency control element comprises frequency modulator coupled to a portion of an output beam from the first laser for tuning the frequency of the portion of the output beam from the first laser and having an electronically adjustable bias for tuning the frequency of the portion of the output beam from the first laser.

13. A method as defined in claim 12, wherein the frequency modulator performs a frequency shift of the portion of the output beam from the first laser.

14. A method as defined in claim 1, further comprising:

storing a spectral signature of a compound;

sweeping the CW radiative beam over at least one frequency band in the range of frequencies from 100 GHz to 1.5 THz; and subsequently determining whether the spectral signature of the compound is present in the acquired spectral information by tuning the frequency of the CW radiative beam in frequency increments less than 100 MHz.

* * * * *